United States Patent [19]
Tucker et al.

[11] Patent Number: 5,235,190
[45] Date of Patent: Aug. 10, 1993

[54] CONTINUOUS AIR MONITORING SYSTEM

[75] Inventors: Richard W. Tucker, Timonium, Md.; John E. McGreevy, McLean, Va.

[73] Assignee: Gemini Research, Inc., Cockeysville, Md.

[21] Appl. No.: 647,558

[22] Filed: Jan. 29, 1991

[51] Int. Cl.⁵ .................................................. G01T 7/04
[52] U.S. Cl. ......................... 250/435; 250/304; 250/364; 250/432 R
[58] Field of Search ............. 250/435, 432 R, 304, 250/364, 370.03, 380

[56] References Cited

U.S. PATENT DOCUMENTS

| | | | |
|---|---|---|---|
| 3,084,255 | 4/1963 | Brinkerhoff et al. | 250/380 |
| 4,090,392 | 5/1978 | Smith et al. | 73/421.5 |
| 4,435,644 | 3/1984 | Heki | 250/435 |
| 4,576,054 | 3/1986 | Lalin | 73/863.03 |
| 4,701,621 | 10/1987 | Kaiser et al. | 250/435 |
| 4,779,466 | 10/1988 | Ramsner et al. | 73/863.33 |
| 4,786,472 | 11/1988 | McConnell et al. | 422/61 |
| 4,800,272 | 1/1989 | Harley et al. | 250/253 |
| 4,868,546 | 9/1989 | Dumbeck | 250/381 |
| 4,920,263 | 4/1990 | Fimian et al. | 250/253 |

FOREIGN PATENT DOCUMENTS 144769  8/1983  Japan ................................. 250/304

*Primary Examiner*—Carolyn E. Fields
*Attorney, Agent, or Firm*—Venable, Baetjer & Howard

[57] ABSTRACT

A continuous air monitor is provided with the capabilities of monitoring certain transuranic and other airborne radioactive particulate with high accuracy and low false alarm rates in the presence of radon and thoron daughter products. A multiple filter sampling approach is used wherein air flow is directed on a alternating basis to each sampling filter in turn. Each filter collects particulate in the size range of interest. Beta and/or alpha activity can be continuously measured on each filter. The air flow can be directed through a chamber where radon and/or thoron gas portions of the air may decay into their daughters and the quantities thereof may be separately measured.

13 Claims, 8 Drawing Sheets

CONTINUOUS AIR MONITORING SYSTEM

BACKGROUND OF THE INVENTION

The present invention relates to a method and apparatus for detecting airborne radioactive contamination, and is particularly concerned with a continuous air monitor (CAM) having the ability to accurately measure transuranic and similar particulate concentrations in the presence of the radioactive decay of naturally occurring inert gasses, such as radon and thoron, and their daughter products (progeny).

The monitoring of airborne radioactive contamination is a critical aspect of the control and/or processing of many materials. One of the areas of technology where monitoring the presence of airborne radioactive contamination is of great concern involves the physical handling and disposing of materials classified as radioactive waste. Other areas of concern relate to weapons manufacturing and the process of nuclear fission, as the byproducts of these respective activities can be quite hazardous. The safety of workers in these areas and of the public in general is dependent on the ability to quickly detect even trace amounts of hazardous radioactive material released into the environment. When safe levels are exceeded, it is desirable to automatically trigger an alarm so as to warn personnel in the vicinity of the radioactive emission, for in some cases automatic or manual emergency procedures must be implemented to combat the emission.

An obstacle to the process of accurately measuring these hazardous materials is the pervading presence of radon and thoron gas and their short-lived daughter products. Both radon and thoron gasses, as well as many of their short-lived daughters, emit alpha energy, whereas other of the daughters emit beta energy. In air monitoring systems which use particulate filters, the daughter products of radon and thoron are collected on the filter paper in addition to other alpha-emitting particles (e.g., plutonium, americium and neptunium) and contribute to the total alpha energy measured on the filter. However, radon and thoron gasses themselves do not collect on the filter paper; instead, they pass through the filter with other gas products. The radon and thoron decay chains are shown in Table I and Table II, respectively.

TABLE I

| Radon Decay Chain | | | |
|---|---|---|---|
| Common Name | Common Symbol | Isotope Name | Isotope Symbol |
| radium | Ra | radium-226 | $^{226}Ra$ |
| radon | Rn | radon-222 | $^{222}Rn$ |
| radium A | RaA | polonium-218 | $^{218}Po$ |
| radium B | RaB | lead-214 | $^{214}Pb$ |
| radium C | RaC | bismuth-214 | $^{214}Bi$ |
| radium C' | RaC' | polonium-214 | $^{214}Po$ |
| radium D | RaD | lead-210 | $^{210}Pb$ |
| radium E | RaE | bismuth-210 | $^{210}Bi$ |
| radium F | RaF | polonium-210 | $^{210}Po$ |
| radium G | RaG | lead-206 | $^{206}Pb$ |

TABLE II

| Thoron Decay Chain | | | |
|---|---|---|---|
| Common Name | Common Symbol | Isotope Name | Isotope Symbol |
| radium | Ra | radium-224 | $^{224}Ra$ |
| thoron | Rn | radon-220 | $^{220}Rn$ |
| thoron A | ThA | polonium-216 | $^{216}Po$ |
| thoron B | ThB | lead-212 | $^{212}Pb$ |
| thoron C | ThC | bismuth-212 | $^{212}Bi$ |
| thoron C' | ThC' | polonium-212 | $^{212}Po$ |
| thoron D | ThD | lead-208 | $^{208}Pb$ |

The III presents the alpha energies and half-lives of materials of typical interest in continuous air monitoring. As a single isotope can exhibit a multitude of decay patterns, the relative percentage of each particular mode of isotope decay is listed under the "comments" column, where appropriate. Such isotopes are commonly referred to as being "multi-modal". Due to rounding errors and the existence of "non-alpha particle-emitting modes of decay" for particular isotopes, the listed percentage for the modes of isotope decay may not total 100%.

TABLE III

| ISOTOPE DATA | | | |
|---|---|---|---|
| Isotope | Half-life | Alpha Energy | Comments |
| $^{222}Rn$ | 3.82 days | 5.490 MeV | Radon |
| $^{218}Po$ | 3.05 minutes | 6.002 MeV | RaA |
| $^{214}Pb$ | 26.8 minutes | no alpha | RaB |
| $^{214}Bi$ | 19.7 minutes | no alpha | RaC |
| $^{214}Po$ | 164 $\mu$sec | 7.687 MeV | RaC' |
| $^{220}Rn$ | 55 sec | 6.287 MeV | Thoron |
| $^{216}Po$ | 150 msec | 6.777 MeV | ThA |
| $^{212}Bi$ | 60.6 min | 6.051 MeV | ThC |
| $^{212}Po$ | 300 nsec | 8.785 MeV | ThC' |
| $^{239}Pu$ | 24,400 years | 5.105 MeV | 12% $^{239}Pu$ |
| $^{239}Pu$ | 24,400 years | 5.143 MeV | 15% $^{239}Pu$ |
| $^{239}Pu$ | 24,400 years | 5.156 MeV | 73% $^{239}Pu$ |
| $^{238}Pu$ | 86 years | 5.456 MeV | 28% $^{238}Pu$ |
| $^{238}Pu$ | 86 years | 5.499 MeV | 72% $^{238}Pu$ |
| $^{241}Am$ | 458 years | 5.443 MeV | 13% $^{241}Am$ |
| $^{241}Am$ | 458 years | 5.486 MeV | 86% $^{241}Am$ |
| $^{243}Am$ | 7950 years | 5.276 MeV | 88% $^{243}Am$ |
| $^{243}Am$ | 7950 years | 5.234 MeV | 11% $^{243}Am$ |
| $^{244}Cm$ | 17.6 years | 5.763 MeV | 23% $^{244}Cm$ |
| $^{244}Cm$ | 17.6 years | 5.806 MeV | 77% $^{244}Cm$ |
| $^{245}Cm$ | 9300 years | 5.362 MeV | 80% $^{245}Cm$ |
| $^{245}Cm$ | 9300 years | 5.306 MeV | 7% $^{245}Cm$ |
| $^{237}Np$ | 2,140,000 yrs | 4.765 MeV | 17% $^{237}Np$ |
| $^{237}Np$ | 2,140,000 yrs | 4.770 MeV | 19% $^{237}Np$ |
| $^{237}Np$ | 2,140,000 yrs | 4.787 MeV | 51% $^{237}Np$ |

With reference to Tables I and III, RaA, RaB, RaC and RaC' have half-lives of less than a half hour. In contrast, RaD has a half-life of 22 years. RaA, RaB, RaC and RaC' are therefore known as the short-lived daughters of radon. Because their half-lives are so much longer than that of the short-lived daughters of radon, the activity of RaD, RaE and RaF can be ignored in typical measurement situations. The final element in the decay chain is lead-206, which is a stable element.

Table III illustrates that the half-lives of the transuranic elements (plutonium, americium and neptunium) are orders of magnitude larger than those of the radon and thoron daughter products. The longest lived of the radon and thoron daughter products, Bismuth-212 (ThC), has a half-life of about one hour (61 minutes). Existing radioactive monitoring applications are constructed in such a manner that the short half-life of the radon and thoron daughters and the long half-lives of the transuranics and other radioactive elements of interest work to the disadvantage of measurement sensitivity and accuracy. The decrease in the sensitivity and accuracy of the radioactivity measurement is due to the rapid build-up of thoron and radon daughter products on the filter area being measured and the high radioactive energy count rate of small quantities of these daughters products compared to other elements such as the transuranic elements present on the filter area which have slower build-up times.

Because of their extremely short half-lives, there is very little $^{214}$Po (RaC'), $^{216}$Po (ThA) or $^{212}$Po (ThC') in ambient air. These elements decay into their immediate daughters almost as quickly as they are formed. Therefore, since these respective isotopes are not in existence long enough to interfere with the radioactive measurements being taken, there is no need to remove them from the air stream to be measured. Furthermore, these isotopes are characterized by relatively high energy alpha emissions in excess of about 6.78 MeV. These energies are well above those of the transuranic elements, which have a peak alpha energy level of about 5.81 MeV. By discriminating the alpha energies, it is possible to recognize the source of the alpha particles. Proper design practices and minimization of filter packing can minimize the effect of counts from these isotopes. The $^{214}$Po can, in fact, provide positive benefits as a marker pulse to indicate energy location and distribution.

The two radon/thoron daughters that cause the most trouble with regard to obtaining an accurate measurement of the radioactive energy present in an air stream, are $^{212}$Bi (ThC) and $^{218}$Po (RaA). These two isotopes have the lowest alpha energies of the radon and thoron daughters and therefore influence the measurement of the transuranic elements the most. In most parts of the country, radon daughters are significantly more plentiful than thoron daughters. Fortunately, because of its short half-life, the contribution of RaA to the total alpha counts generated by radon daughters is only about 10% of the total. Although alpha counts attributable to RaA constitute a relatively minor portion of the total radon daughter alpha energy collected on a filter paper, these counts can still be much more numerous than those that are attributable to the transuranic counts. There have been several techniques that have been developed in an attempt to separate the radon and thoron daughters from the sample air stream prior to its passage to the filter. However, most of these techniques involve somewhat complicated air flow and equipment configuration.

In relatively clean particulate environments, an appreciable portion of the RaA is not attached to dust particles. Typical fractions of unattached RaA are in the range of from about 50% to about 90%. However, the fraction of RaA that is unattached can vary considerably in accordance with the amount of particulate material in the sample of air that is being tested. In accordance with the design of the air particulate collection system, some of the radon and thoron progeny can be removed. Plates and screens (both charged and uncharged) have previously been used to remove a portion of the radon daughter products before they are able to deposit on the filter paper. None of these known removal methods is 100% effective, however, and an appreciable percentage of the radon and thoron daughter products pass through to the filter paper. For example, employees of various government regulatory agencies have for some time used simple wire mesh (on the order of 60×60 per inch) to remove major portions of the unattached RaA.

The current detection requirement in many localities for work-place and stack emissions for plutonium (a common transuranic element of interest) provides for a DAC (derived air concentration) level of $2 \times 10^{-12}$ $\mu$Ci/ml ($2 \times 10^{-3}$ pCi/l). The DAC level for radon and its daughters is set at $3 \times 10^{-8}$ $\mu$Ci/ml (30 pCi/l). Actual radon levels in above-ground facilities are seldom above 4 pCi/l and are usually at or below 2 pCi/l. Even at 2 pCi/l however, the radon alpha activity is three orders of magnitude higher than that for plutonium.

As has been noted above, efforts are usually undertaken to discriminate between the particle energies emanating from the radon and thoron daughters and the particle energies emanating from the primary particles of interest (e.g., transuranics) when attempting to monitor the levels of airborne radioactive contaminants. In some cases, the energies that are to be monitored are divided into two spectrums. However, this approach has been found to be too inaccurate for the reasons specified above. Alternative monitoring techniques using multichannel analysis are frequently used in present particle energy discrimination applications. The typical multichannel analyzer divides energies to be monitored into 256 individual energy ranges. As noted above and in Table III, the highest alpha energy levels of the emissions of the transuranic materials are less than that of the lowest energy alpha particle emanating from the short-lived radon and thoron daughters. However, because of physical geometries, detector imperfections, particle burying into the filter paper, and particle covering by dust on the filter paper, the precise and repeatable measurement of particular alpha energies can be compromised, the aforementioned disparity in energy levels for the emissions of the transuranic and radon and thoron decay products notwithstanding. The energies of some of the lower radon and thoron daughter product alpha energies may be measured within the energy range of the higher energy transuranic alpha particles, thereby resulting in the generation of false alarms which can have adverse and costly consequences. These shortcomings have led to the development of the continuous air monitoring system of the subject application.

SUMMARY OF THE INVENTION

In accordance with the present invention, the limitations of the prior art are avoided by the provision of a continuous air monitoring (CAM) device which uses multiple sampling filters to alternately sample the air of a chosen environment. The CAM device of the present invention allows the level of transuranic elements to be accurately measured even in environments contaiing high levels of radon and thoron gas. The data collected in this manner is analyzed to calculate the separate contribution that is attributable to each of the radioactive components that are of interest, such as radon, thoron, radon and thoron progeny, and the transuranics.

In an aspect of the present invention a continuous air monitoring system comprises an air intake port and at least two air filtering means positioned in fluid communication with the air intake port. In addition, the system includes selection means for selectively supplying air from the air intake port to a predetermined one or more of the filtering means and detection means positioned relative to the filtering means for measuring the level of radioactivity of particles collected by the filtering means.

BRIEF DESCRIPTION OF THE DRAWINGS

The various objects, advantages and novel features of the invention will be more readily apparent from the following detailed description when read in conjunction with the appended drawings, in which.

DETAILED DESCRIPTION OF THE PREFERRED EMBODIMENT

The preferred embodiments of the present invention are oriented to the measurement of plutonium (often found as an oxide) in the presence of radon gas. The application of the apparatus and method of the subject invention to the measurement of other airborne elements and corrections for thoron gas in addition to radon are similar to that described below, but may result in different filter sampling timing and the number of filters to be used.

One aspect of the invention applies a multiple sampling filter and detection system for measuring the emissions activity of radioactive material that is trapped on each filter, whereby one filter samples air during a prescribed time interval while other filters are inactive. A prescribed time interval is given for the short-lived radon and thoron daughter products to decay on the filter(s) not currently sampling air, leaving primarily long-lived products to be measured on the filters.

Separate sampling heads are provided and the air flow path is switched between the sampling heads. An energy measurement device is associated with each filter, including the particular filter through which air is being drawn. In both situations, the energy emissions from radioactive material trapped by the respective filters is constantly recorded.

The principles of radioactive particle accumulation on a filter paper are used to maximum benefit in the subject invention. The build-up of a single independent radioactive element on a filter paper is determined by the function:

$$I = Q^* C^* (1 - e^{(-t/\tau)})$$ Equation 1 where
$I$ = filter activity in pCi
$Q$ = flow rate in l/min
$C$ = isotope concentration in pCi/l
$\tau$ = the mean life in minutes
$t$ = the elapsed time in minutes Any consistent set of units may be used in the equation. For example, "I" could be dpm (disintegrations/minute) and "C" could be dpm/l.

The mean life $\tau$ is a value that is 1.44 times the isotope half-life. RaA has a half-life of 3.05 minutes and therefore a mean-life of 4.39 minutes. An activity level of 4.44 dpm/l occurs when a radon concentration of 2 pCi/l exists. In the instance of a sample of air containing only RaA at a concentration of 2 pCi/l being taken at a rate of 10 l/min, Equation 1 would yield a filter activity of 30.2 dpm after 5 minutes, 39.8 dpm after 10 minutes, and 44.35 dpm after a period of 30 minutes. Following passage of an extended period of time, the filter activity would reach a steady rate of about 44.4 dpm. This steady condition is known as equilibrium. It takes only 3 mean-lives to reach 95% of the final (equilibrium) activity. In the case of RaA, this equilibrium state is attained in 13.32 minutes.

For very small values of $-t/\tau$, the value of $1 - e^{(-t/\tau)}$ is approximately equal to $t/\tau$. Equation 1 then simply becomes:

$$I = Q^* C^* (t/\tau)$$ Equation 2

Figure 1:
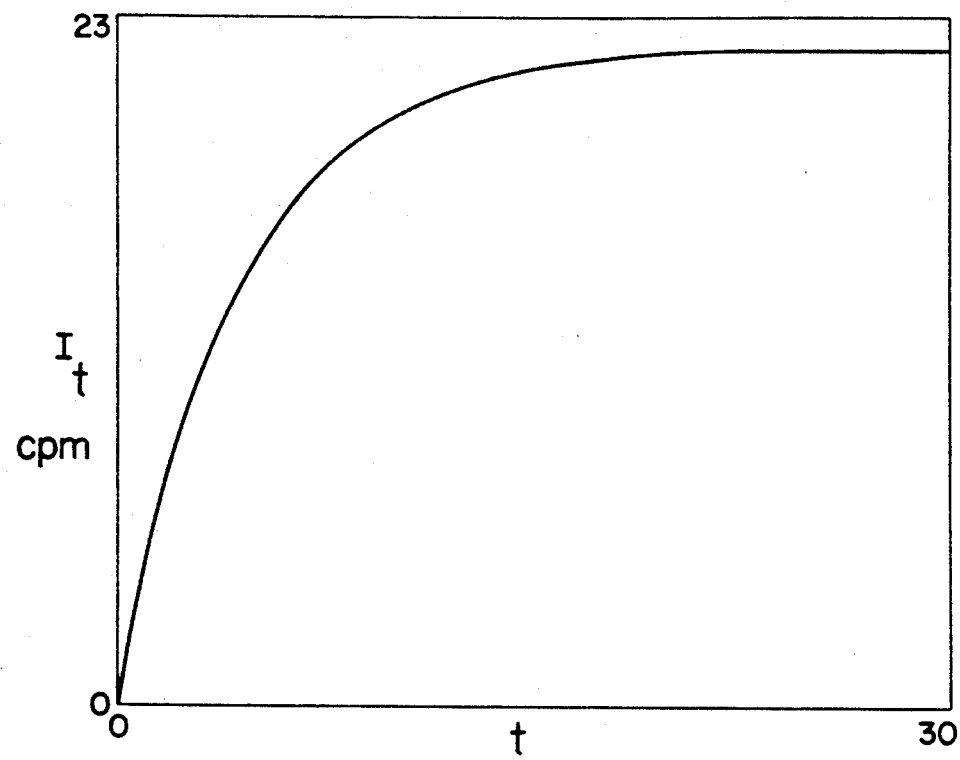
FIG. 1 shows the build up of alpha activity on a filter for short lived radioactive elements for constant air flow through the filter and constant concentration of that element in the air.
Figure 2:
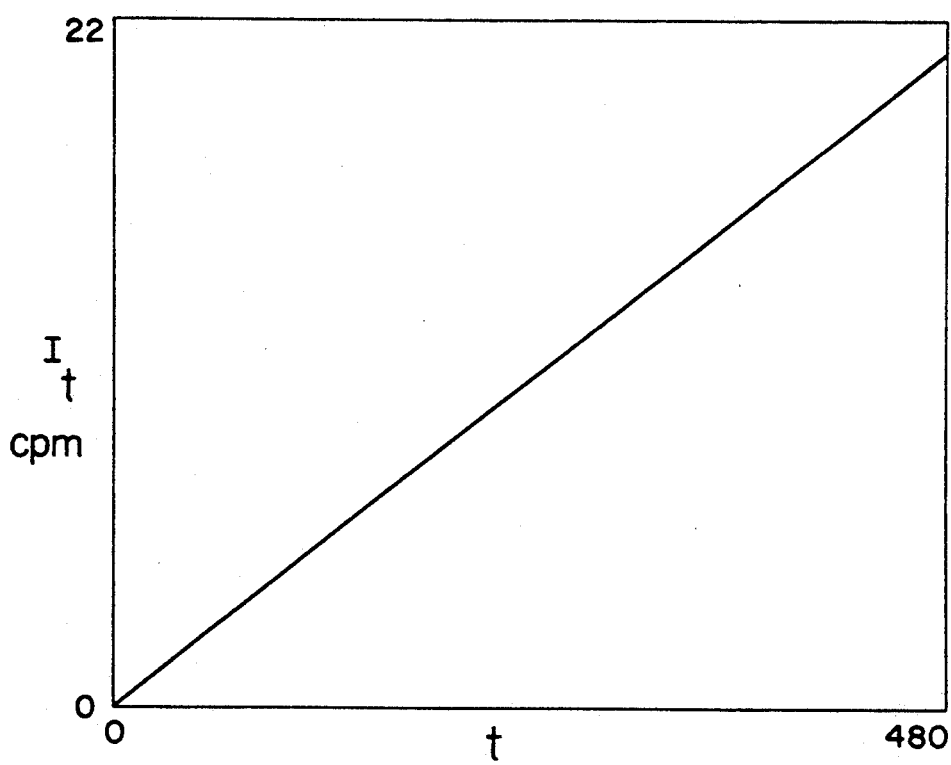
FIG. 2 shows the build up of alpha activity on a filter for long lived radioactive elements for constant air flow through the filter and constant concentrations of that element in the air.

This requires the growth on the filter for long half life elements (e.g., plutonium) to be a purely linear function for periods of up to months or years. The growth in activity on a filter paper of a short-lived element is shown in FIG. 1, where $Q = 10$ l/min, $C = 2.2$ pCi/l, $\tau = 4.39$ min, and $t = 0$ to 30 min. The growth in activity of a long lived element is shown in FIG. 2, for which Equation 2 is applicable. Accordingly, $Q = 10$ l/min, $C = 0.0044$ pCi/l; and $t = 0$ to 480 min.

Radioactive decay occurs on a filter when the source of new radioactive particles to the filter ceases, specifically when the air flow is interrupted. Such decay can be regarded as the inverse of filter build-up. The controlling relationship then becomes as follows:

$$I = C_o^* e^{(-t/\tau)}$$ Equation 3 where $C_o$ = the initial activity or concentration, typically measured in dpm.

Figure 3:
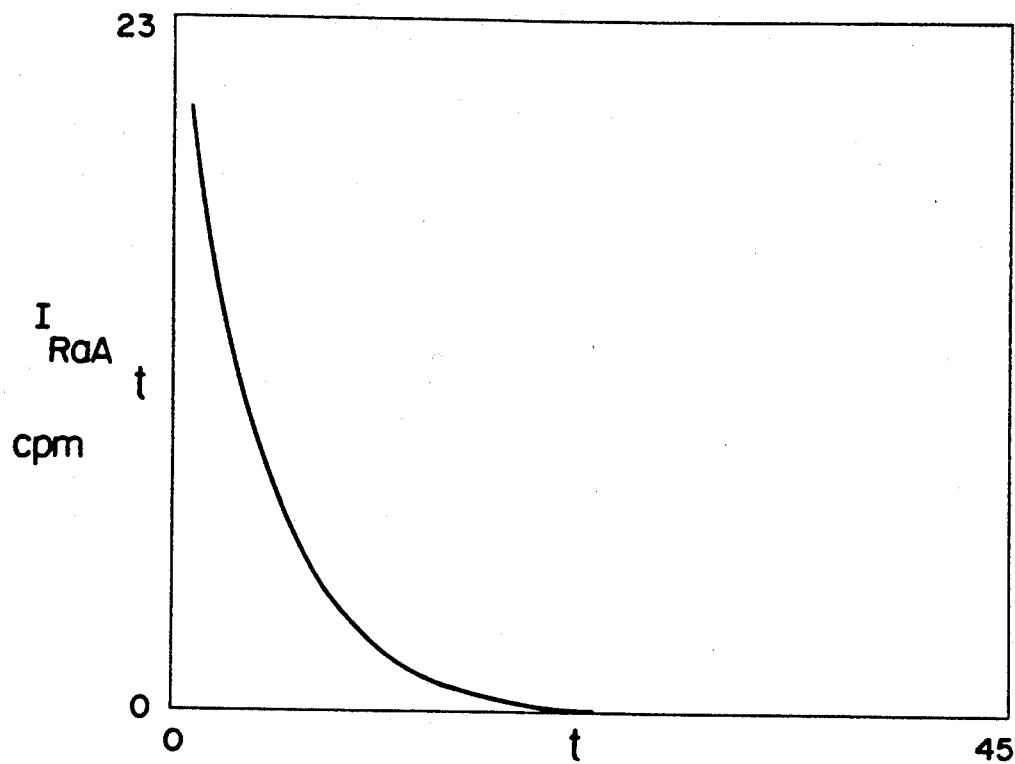
FIG. 3 shows the decay of alpha activity on a filter when the air flow is removed for a short-lived radioactive element.
Figure 4:
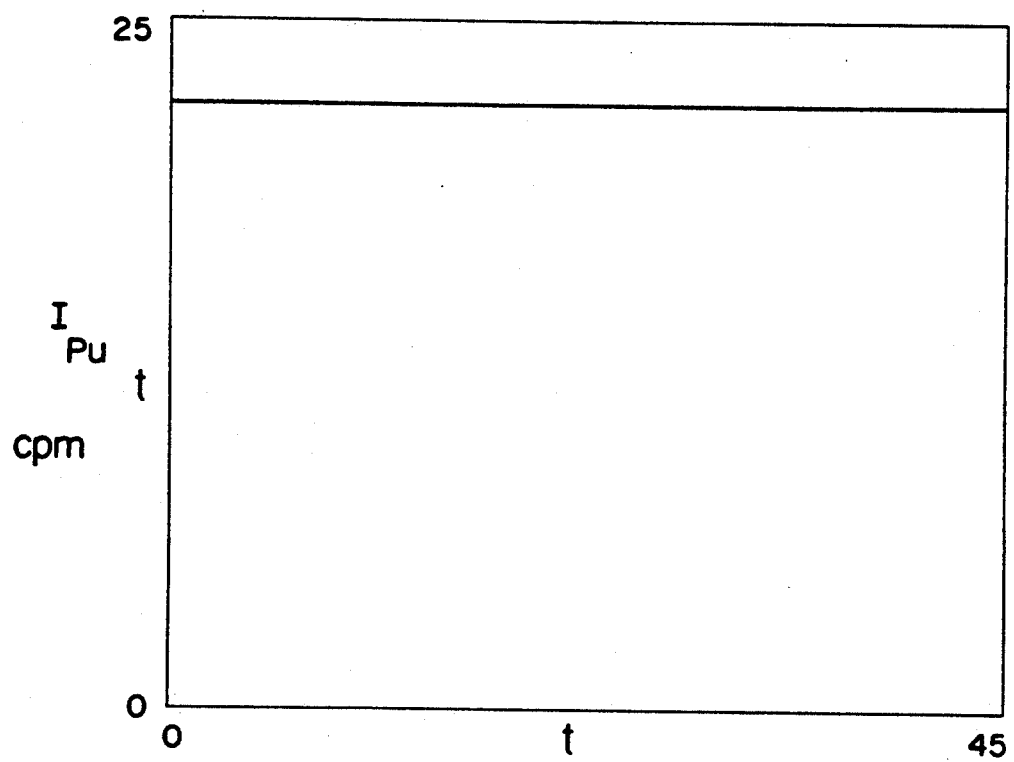
FIG. 4 shows the decay of alpha activity on a filter when the air flow is removed for a long-lived element.

A total of three mean-lives is required to ramp-up to 95% of the final value for filter activity build-up. Likewise, a total of three mean-lives is required for the decay of 95% (5% remaining) of the initial activity or concentration. For the case of the transuranic isotopes having long mean-lives, there will be no appreciable decrease in the filter activity after the source of new particles is removed. The foregoing differences in decay rate are illustrated graphically in FIGS. 3 and 4. In FIG. 3, there is shown decay of RaA, a short-lived isotope having a half-life of 3.05 min. Applying the relationships set forth in Equation 3 above to RaA, $C_o=25$ pCi/l, $\tau=4.39$ min, and $t=0$ to 45 min., an exponential decay curve results as depicted in the drawing. In FIG. 4, there is shown the decay curve for $^{239}$Pu, a long-lived isotope having a half-life of 24,400 years. Utilizing the relationship of Equation 3, in which $C_o=22$ pCi/l, $\tau=1.82\times10^{10}$ min, and $t=0$ to 45 min., an essentially flat, zero decay graph as shown in FIG. 4 results.

This invention separates the effects of the transuranic elements from the radon and thoron elements and their respective progeny by utilizing: 1) the linear activity build-up under constant input air flow conditions for the transuranic elements (FIG. 2); 2) the virtual absence of decay activity when there does not exist an incident air flow for the transuranic elements (FIG. 4); and 3) the rapid decay of the activity of the radon and thoron daughters after removal of the incident air flow (FIG. 3).

The operation and benefits of the multiple filter arrangement of the subject invention with time periodically allocated for filter stabilization can be seen most clearly in a multichannel analyzer view of the process, as illustrated in FIGS. 5 through 8.

Figure 5:
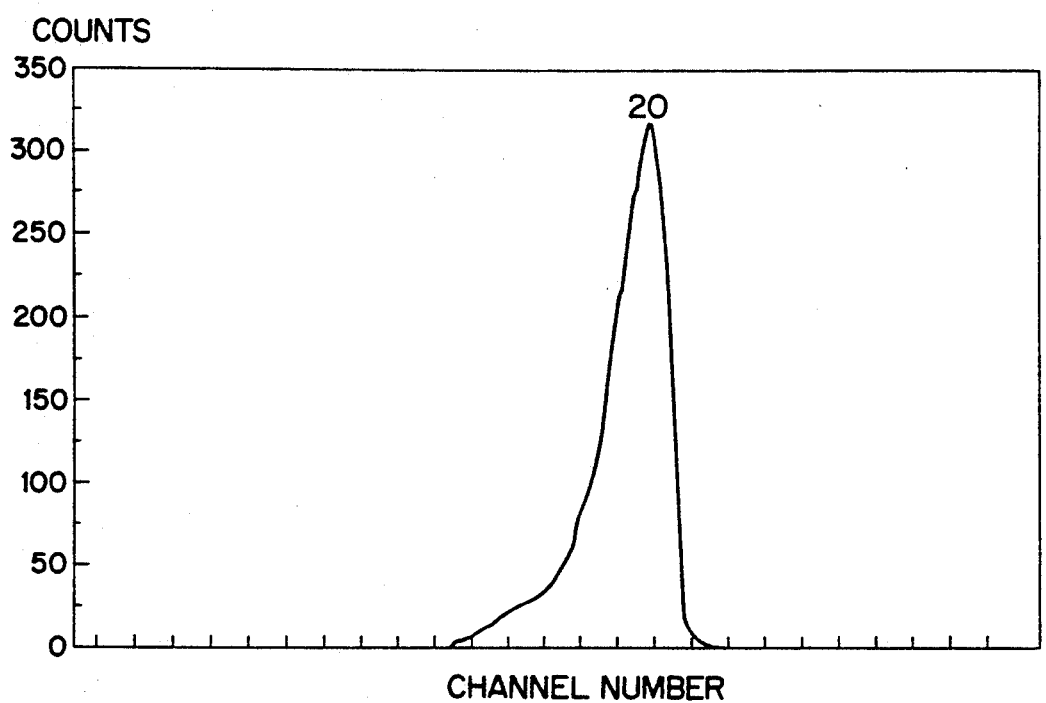
FIG. 5 illustrates the typical multichannel analyzer response to a single radioactive element.

FIG. 5 illustrates the energy spectrum typically measured by a multichannel analyzer for a filter paper containing only RaC'. RaC' has the highest energy alpha particle in the radium-226 decay chain. The angle from the peak 20 to the baseline at the right of the peak is fairly sharp. In contrast, the tail portion of the graph that extends from the peak leftward is much less sharp and is more generally ill defined. This tail portion results from the attenuation of alpha particles generated by the decay of RaC' prior to reaching the detector. This attenuation is the result of alpha particle burying in the filter paper, dust covering of the filter paper, and longer paths taken from the point of alpha particle emission to the detector surface.

Figure 6:
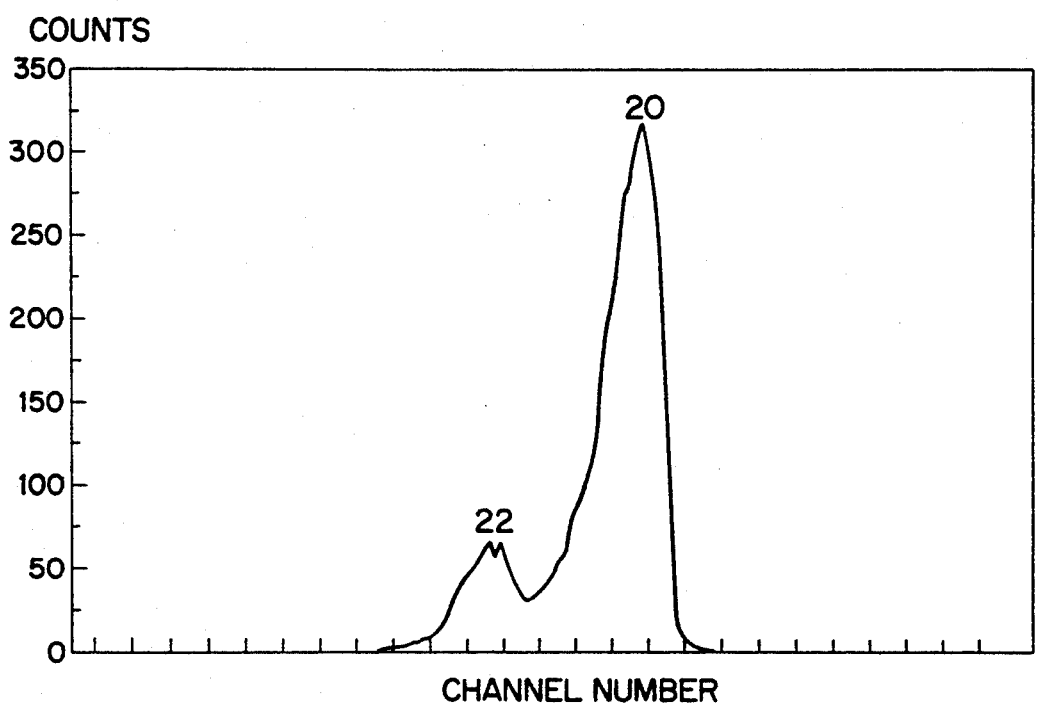
FIG. 6 illustrates the typical multichannel analyzer response to the presence of different radioactive elements such as RaC' and RaA.

FIG. 6 illustrates the energy spectrum typically measured by a multichannel analyzer for a filter paper containing all of the radon daughter products. The rightmost (and highest count) energy peak 20 is attributable to RaC', whereas the left peak 22 is attributable to RaA. The left tail of the RaC' alpha energy extends partially into the RaA energy band due to the presence of overlapping energy emissions that arise from particle attenuation in the manner described above.

Figure 7:
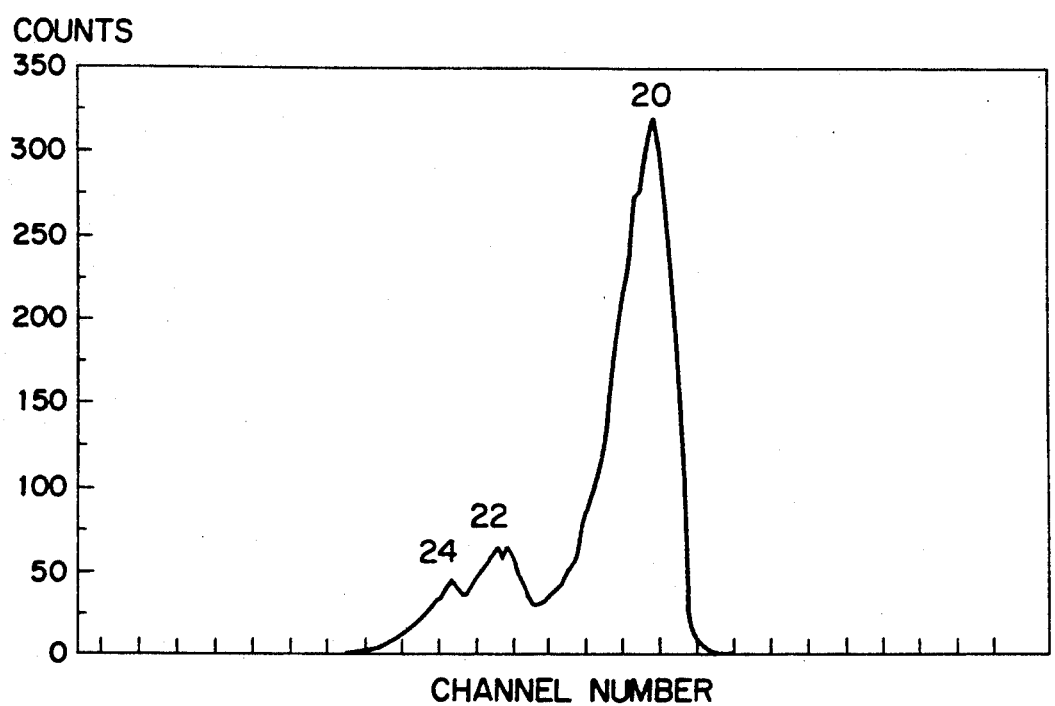
FIG. 7 illustrates the typical multichannel analyzer response to the presence of three different radioactive elements such as RaC', RaA and Pu, where the peak values of two of the alpha energies are relatively close to one another.

FIG. 7 illustrates an energy spectrum that is similar to the spectrum in FIG. 6, with the addition of plutonium on the filter paper. The relatively weak, left-most peak 24 corresponds to energy emissions from plutonium. As can be seen in the drawing, this relatively weak peak from the plutonium is nearly indistinguishable from the tail portion that is attributable to RaA. Unfortunately, this drawing graphically illustrates the typical energy emission spectrum for the typical airbourne concentrations for which it is most desirable to trigger an alarm indicative of the presence of plutonium.

Figure 8:
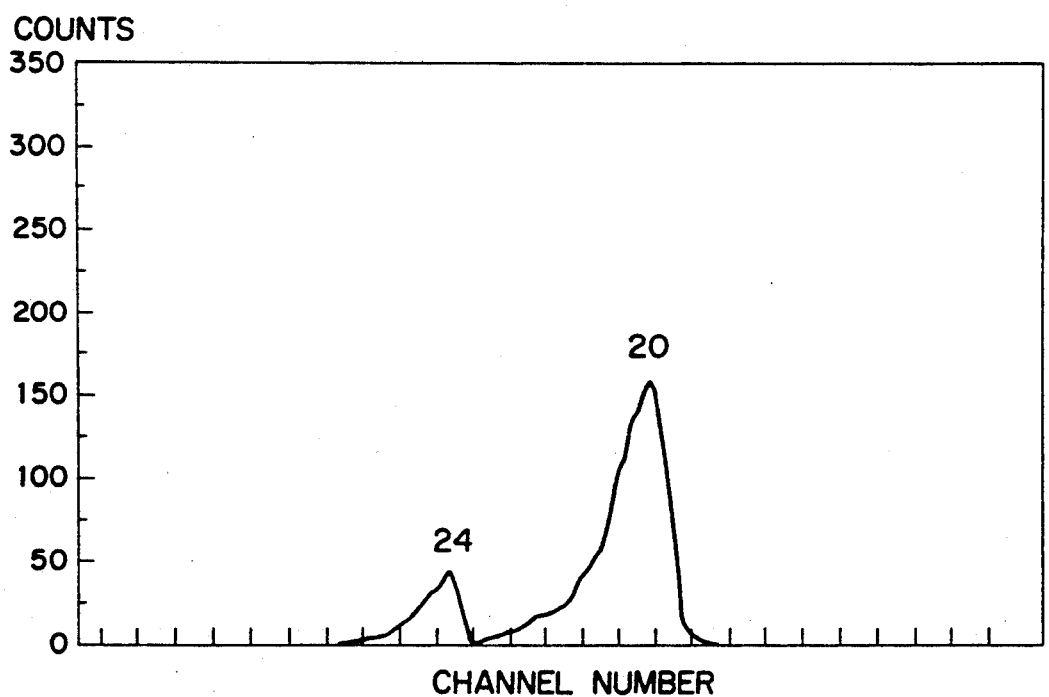
FIG. 8 illustrates the typical multichannel analyzer response after a 30 minute cool down period has elapsed after the removal of air flow through the filter.

FIG. 8 illustrates the energy spectrum for an air sample of the type which exhibits an energy spectrum illustrated in FIG. 7 following the suspension of air flow thereto for a period of about 30 minutes. At the point at which the air flow was removed, the energy spectrum would have been substantially similar to that as shown in FIG. 7. Following the passage of about 30 minutes, nearly seven mean lives of RaA have passed, and nearly all RaA emission activity has ceased. The RaC' count peak 20 is also notably diminished. The tail portion of the RaC' graph has almost no effect in the region of the plutonium peak 24. Because of the distance between the two peaks 20 and 24, the shape of the RaC' peak 24 can be computed and the counts due to the integral of the area of the RaC' peak that lies in the plutonium region can be calculated to provide a correction for the nominal background effect in that region.

The foregoing manner of processing allows for the counting in the plutonium energy region to be precisely determined without the hinderance of background counts. This processing arrangement is quite advantageous, for it allows the continuous air monitor of the subject invention to achieve unprecedented sensitivity with typically encountered air flow rates of from about 25 lpm to about 50 lpm. Alternatively, the foregoing processing arrangement permits for the use of substantially reduced air flow rates while still achieving levels of sensitivity comparable to that of prior art implementations.

A second aspect of this invention, which provides for the correction for the effects of radon and thoron gas products, a measurement device is inserted into the flow path after the particulate material is removed from the air by a sampling filter. This measurement device could be in the form of a dual filter measurement device or a scintillation cell. Portions of the radon and thoron gas which enter either of these measurement devices will decay into their daughter products. The decay of some of these elements will result in the release of alpha particles, which can be measured directly with a solid state detector in the dual filter method, or indirectly, through the detection of light flashes caused by an alpha particle striking scintillation material in the scintillation cell. The amount of radon or thoron measured in this manner can be used as an estimate of the amount of radon and thoron daughter products collected on the primary sampling filter, and corrections can be implemented in the measurement of the particles of interest.

Figure 9:
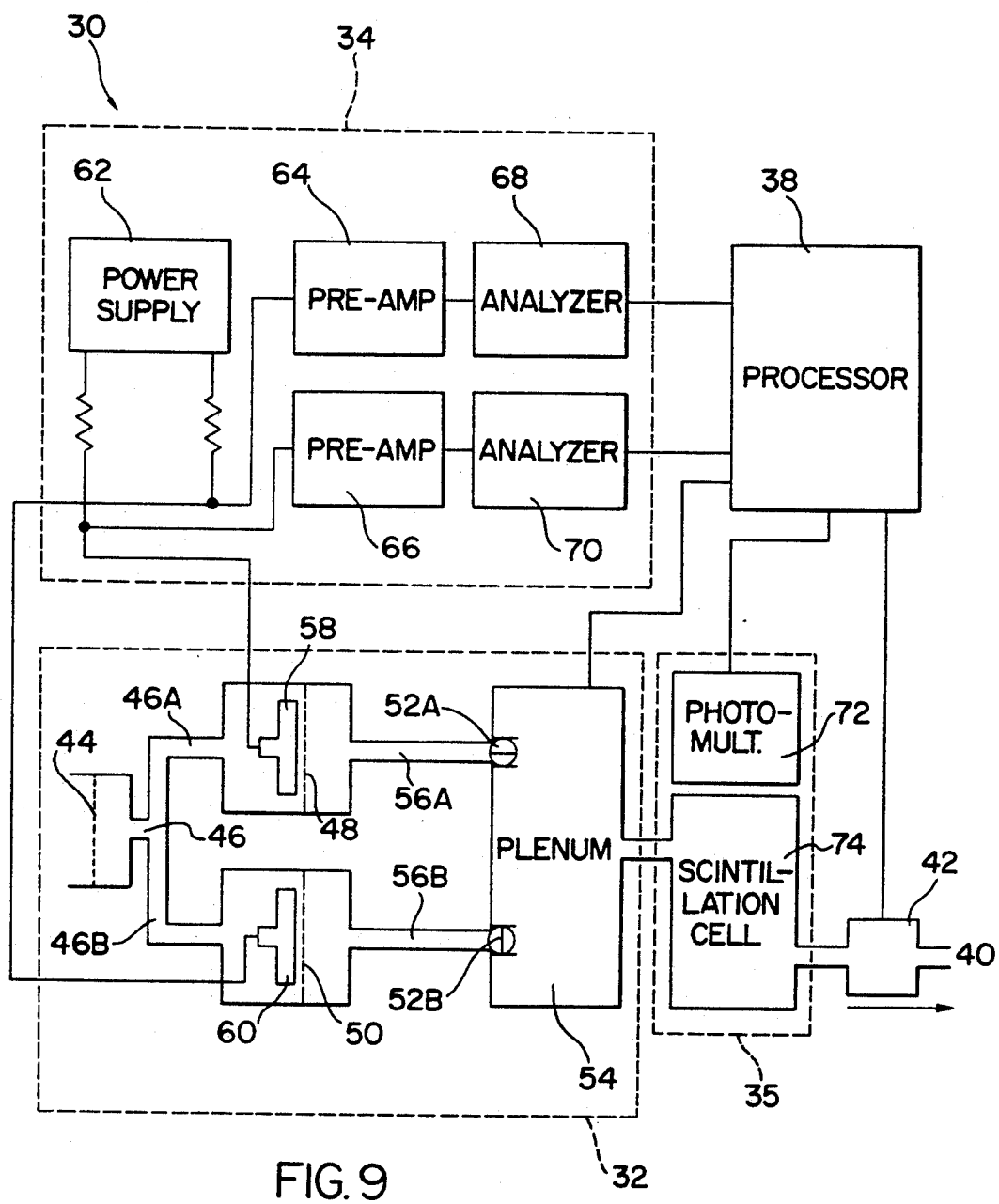
FIG. 9 is a schematic diagram showing the major components of the monitor of the subject invention.

FIG. 9 illustrates the interrelationship between the major system elements of the continuous air monitor of the subject invention. In the drawing, the continuous air monitoring system, which is designated generally by reference numeral 30, is comprised of four general components: an air sampling assembly 32, detector electronics 34, a secondary radioactive gas measurement unit 36, and a processor unit 38. The sampling assembly 32 is preferably placed in a location of critical importance (e.g., at or near a worker area) or in a location where the release of harmful elements into the air are likely to be quickly detected (e.g., near room air intake ducts). The detector electronics 34 are preferably placed within the same enclosure as the sampling assembly 32 to ensure low noise and high quality pulse transmission. The secondary radioactive gas measurement unit 36 and processing unit 38 may be positioned apart from the detector electronics 34 and the sampling assembly 32, but are co-located therewith in the preferred embodiment. The processor unit 38 includes a microprocessor with an internal clock as well as connection ports for input/output peripheral devices such as a keyboard which may be used to input desired operating parameter.

The air outlet 40 is connected to a negative pressure generating means (not shown). This connection can be in the form of a shop air connection or may be supplied by a pump. The air flow rate is measured by a digital flow meter 42 and the flow rate digitally transmitted to the processor unit 38. This sampled flow rate is used in the computation of the radiation levels sampled on the filters in the manner described below.

As the air enters the sampling assembly 32 in the direction of arrow A, it passes through a wire mesh screen 44, which is provided to remove predetermined radon daughters from the air stream. This removal process operates through the principal of charged particle attraction. Because of the closeness in the alpha energies released by plutonium and RaA (5.1 MeV and 6.0 MeV, respectively), it is the removal of RaA that is of greatest interest. RaA is the first daughter of radon gas and, because of the release of an alpha particle incident to its formation, is in the form of an ion with an atomic charge of $-2e$. Because of this negative charge, RaA is highly attractive to other materials. However, because RaA has such a short half life (3.05 minutes), many of the RaA ions do not have time to bond to any other particles before they decay into the next daughter product (RaB). As the RaA ions pass near the wire mesh screen 44 they are attracted to the screen. Some of the unattached RaA ions attach to the screen 44 and are removed from the air flow. The removal efficiency of the RaA ions can be quite variable and depends on factors such as humidity, air particulate concentrations, and air sampling rates. Efficiencies of upwards of 90% or better can be attained under favorable circumstances. Removal of other ionized radon daughter products is also possible; however, removal efficiency is usually somewhat lower than that due to RaA as a result of the much higher probability of being attached to dust or other particulate matter prior to arrival at the screen 44.

After passing through the radon daughter screen 44, the input air is drawn through an air channel 46 that is bifurcated at its distal end to form passges 46A and 46B to one of the two particulate filters 48 and 50 in accordance with the setting of valves 52A and 52B associated with plenum 54. The valves 52A and 52B communicate with their respective filters 48 and 50 through corresponding air channels 56A and 56B. System operation begins by drawing air through one of the filters, such as filter 48, for a predetermined period of time. Time periods of operation may vary in accordance with the operational environment and particular isotope under study; however, for the preferred embodiment where RaA is believed to constitute the main background problem, a complete cycle time (one "on" and one "off" period for each filter) of from about 30 minutes to about 120 minutes is appropriate. A 90 minute cycle is used in the preferred operational scheme of the subject invention, in which case air is drawn through the filter 48 for about 45 minutes, after which air flow to the filter 48 is terminated. Incoming air is then drawn through the second filter 50 for another 45 minute sampling period, and the air drawn through the respective filters is processed in the manner described below.

Solid state alpha particle detectors 58 and 60, such as the model 500-PNA detector manufactured by Applied Electron Corp. of Santa Clara, Calif., U.S.A., are preferably positioned directly above the collection surface of the filters. Each of these diffusion detectors has a surface area of about 500 mm², is reversed biased, and provides an alpha particle stopping area of at least 100 $\mu$m to ensure complete energy absorption. The number of free electrons generated in the detector by each alpha particle, as it relinquishes its energy to the detector 58 or 60, is proportional to the energy of the alpha particle as it enters the detector. The magnitude or height of the output pulse is therefore proportional to the alpha particle energy. A high voltage power supply 62 supplies DC reverse bias to the detectors 58 and 60. Signal preamplifiers 64 and 66 are connected directly to the detectors 58 and 60 to generate an output pulse height of about 2 volts for plutonium alpha strikes. A multichannel analyer 68, 70 is arranged to receive signal output from a corresponding signal preamplifier 64, 66. Output from the analyers 68 and 70 is directed to the processor unit 38 for processing thereby in accordance with a predetermined processing scheme stored in associated processor memory.

The gas measuring unit 36 is comprised of a high gain photomultiplier tube 72 such as the model R268 photomultiplier manufactured by Hammamatsu Corp. of Bridgewater, N.J., U.S.A. and a flow-through scintillation cell 74 such as the model RA-304 manufactured by Rocky Mountain Scientific Glass Blowing Co., of Denver, Colo., U.S.A.. In the scintillation cell 74, some of the radon gas decays into RaA, resulting in the emission of an alpha particle in the process. Most of the RaA formed in this manner will deposit on the sides of the cell and continue to decay through the other daughter products. Alpha particles will also be emitted by the RaA and RaC' isotopes. When an alpha particle strikes the luminescent material that coats the interior walls of the scintillation cell 74, light flashes are produced. These light flashes are detected by the photomultiplier tube 72 and counted by the procesor unit 38. Output from the scintilltion cell 74 is directed to the flow meter 42 for quantification as to volume of air flow through the cell 74. Signal output from the flow meter 42 is also directed to the processing unit 38 for processing along with data received from the sampling and electronics assemblies 32 and 34, respectfully, thereby allowing for the rapid detection of increses in radon levels and appropriate consideration factors of related to these increased detections.

Figure 10:
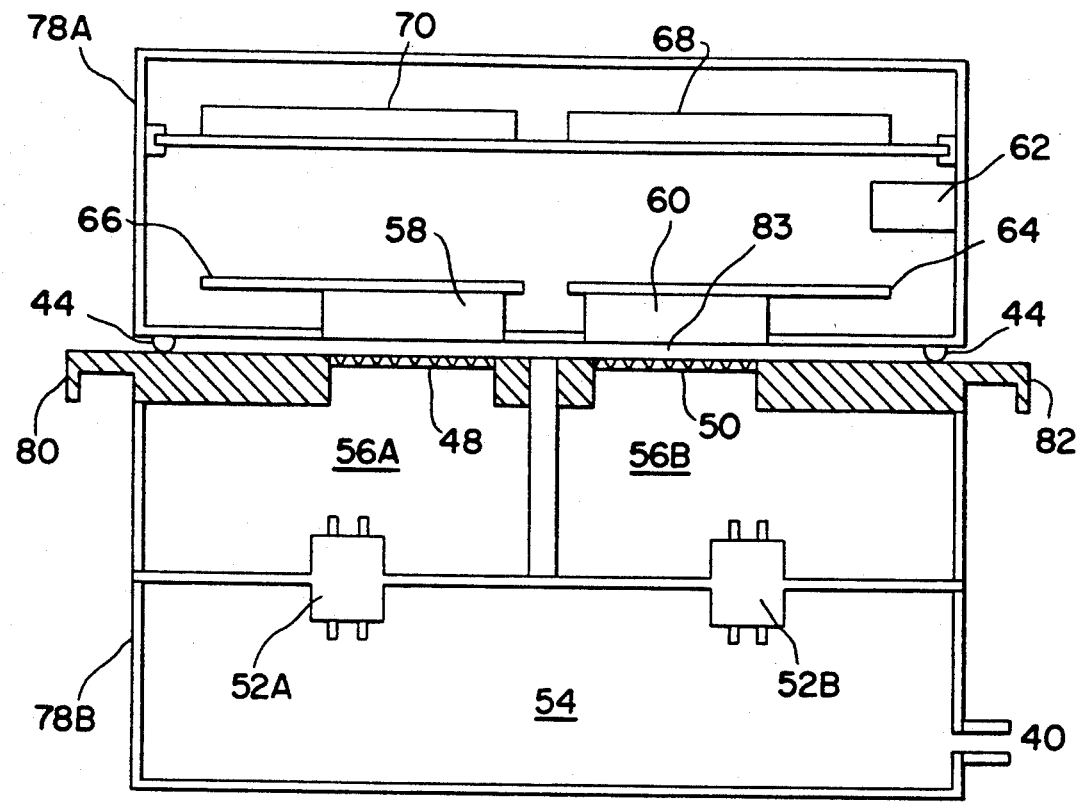
FIG. 10 is an illustration of the sampling head assembly for the preferred embodiment of the subject invention.

FIG. 10 shows a vertical center cross sectional view of the air sampling assembly 32 of FIG. 9. The assembly 32 includes a radial entry sample head 78 having two filter holder assemblies 80 and 82 which insert from opposing sides of the head. The detectors 58 and 60 (FIG. 9) are positioned in the upper portion 78A of the head, whereas their corresponding filters 48 and 50 are positioned in the lower portion 78B of the head 78 directly below the detectors. There is provided a gap 83, optimally about 4 mm in height, between each filter and the surface of its corresponding detector. The wire mesh radon daughter screen 44 surrounds the opening around the perimeter of the monitoring device to filter air before it is drawn into the device. The various components of the detector electronics unit 34 are also positioned in the upper portion of the sample head.

The air flow path in FIG. 10 begins with air entering the head 78 of the air sampling assembly 32 through the radon daughter screen 84 mounted to the perimeter of the assembly. If the orientation of valve assembly, including valves 52A and 52B, is such that valve 52A is open and valve 52B is closed, the air will flow through filter 48, channel 56A, valve 52A, into plenum 54 and out through air outlet 40. When the orientation of the valves 52A and 52B is reversed, air is directed to filter 50, through channel 56B, through valve 52B, into plenum 54 and out through outlet 40.

Figure 11:
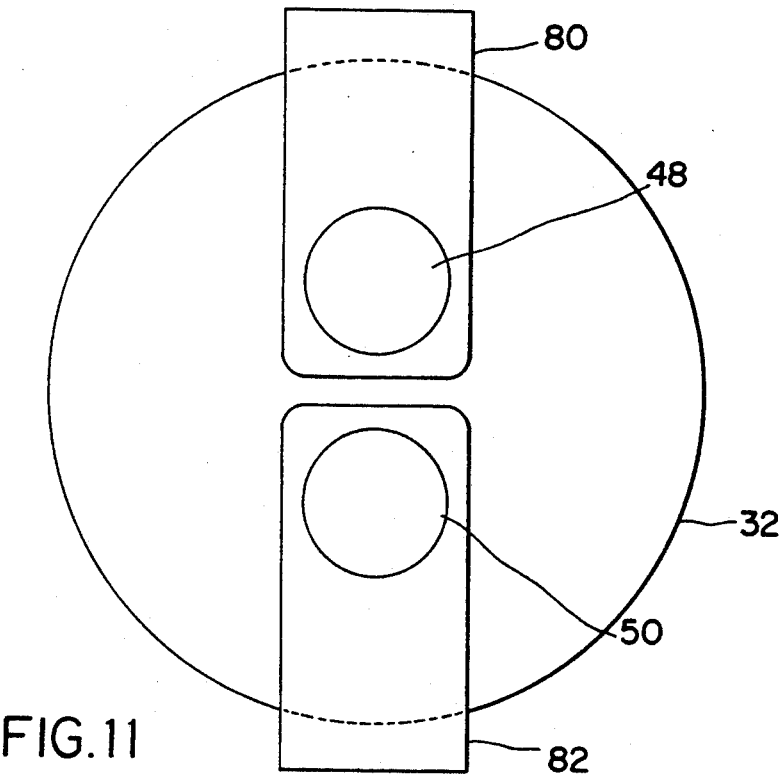
FIG. 11 is an illustration of the preferred embodiment of the lower portion of the sample head containing a two filter system.

FIG. 11 shows a top view of the physical layout of the lower portion 78B of the sample head 78 in the preferred embodiment.

As noted previously, output from the preamplifiers 64 and 66 is routed to a corresponding one of the multichannel analyzers 68 and 70. In the preferred embodiment, each multichannel analyzer comprises 256 channel devices. When a pulse has been sampled by one of the multichannel analyzers, an alpha energy spectrum is produced and an interrupt is generated thereby and sent to the processor unit 38, after which the processor unit reads the channel number from the analyzer 68, 70 which generated the interrupt request.

The processor unit 38 stores the alpha energy spectrum that is generated in this manner by sample period. This energy spectrum is constantly monitored to determine the plutonium concentrations in the air. At any moment, the processor unit has access to the energy spectrum for past sample periods and is continually adding to the energy spectrum for the current period for both the active (sampling channel) and for the inactive (cooling down) channel.

The contribution of the RaA to the samples taken in the last 20 minute portion of the 45 minute inactive period in the region of the transuranics' alpha energy would be expected to be less than about one percent (1%) of what it was at the time when the flow to the associated filter and detector was removed. After the first approximately 25 minute portion of the 45 minute mesuring interval, the RaA activity is only about 0.3% of its value at the time that the air flow was removed. After 45 minutes, the remaining RaA is only about 0.004% of the original value. On the average, the RaA contribution is reduced about three orders of magnitude during this forty-five minute sampling period.

The activities of the other radon daughters are, of course, also reduced during this sampling time period, but not as dramatically as that experienced by RaA. The other major alpha contributors, RaB and RaC (with their RaC' daughter), have mean-lives of 26.8 and 19.7 minutes, respectively. Over the 45 minute sampling period, their respective activity levels will be reduced to about 30% of their initial values.

In addition to the reduction of the interfering radon daughters during this cooling down (inactive) time period, the decay rates that are measured in each energy region of interest by the multi-channel analyzer yield additional data concerning the amount of activity according to decay rates. That is, each isotope has its own half-life which determines its own ramp-up and ramp-down characteristics (i.e., activity changes during the active (air flow) and inactive (non-air flow) periods). By analyzing the ramp-up and ramp-down time constants, additional data concerning the composition of the changing activity can assist in identifying the actual quantity of each of the active isotopes present in the measured air sample.

There are several significant benefits resulting from the foregoing approach. Because the ratio of plutonium alpha energy to RaA energy is improved by about three orders of magnitude by the apparatus and method of the subject invention, the sensitivity toward measuring plutonium activity is greatly enhanced. This sensitivity enhancement can result in a decrease in air flow requirements in order to meet the overall detection requirements. Furthermore, filter life can be increased by the use of two filters and reduced air flow. The ensuing decrease in the occurrence of "filter packing" (i.e., obtruction of filter pores due to dust and other particulate matter) that results from operation of the filters in the foregoing manner will reduce the size of the tail portion of each particle's alpha energy emission spectrum and increase the ability of the multichannel analyzer (68 and 70) to distinguish between adjacent alpha energy bands.

The air flow is directed through a predetermined one of the filters 48 and 50 through appropriate manipulation of selector valves 52A and 52B. The operation of these valves is controlled by the processing unit 38 in a conventional manner, which causes these valves to toggle state every 45 minutes.

Radon levels can increase over a period of only several hours, but unusual atmospheric conditions will occasionally cause large rises in the radon level in a period of only a few minutes. In these rare cases when a rapid radon buildup occurs within a 45 minute active sampling period, it becomes difficult to distinguish a sudden increase in radon level from a sudden increase in plutonium level.

It will generally take from one to two hours for the RaB and RaC isotopes present in the sampled air to reach a new equilibrium (i.e., equilibration between particle decay and rate of collection of new particles) following a radon gas burst. However, equilibrium is reached for RaA within a period of about ten minutes. The injection of a burst of radon gas will first produce a substantial increase in the level of RaA, which is sequentially followed by increases in the level of RaB, RaC, and RaC'. RaC' activity can lag the radon gas and RaA' activity by many minutes. During the course of this lag interval, there can be a burst of emissions activity in the area of about 6.0 MeV. The question then arises, is this increased activity due to the presence of plutonium or radon? The multi-channel analyzer can help in this decision but, as shown earlier, the difference between the RaA alpha energy and the plutonium alpha energy is close enough to cause overlap from the RaA emission spectrum tail. The addition of a radon gas measurement cell in-line with the filtered air provides the additional information needed to eliminate false alarms by providing up-to-date information on changes in radon gas levels. For example, an activity spike in the sampled air emission spectrum in the range of about 5.5 MeV to about 6.0 MeV accompanied by a proportional increase in the radon gas measurement would not require an alarm, whereas the triggering of an alarm would be appropriate if there had been no increase in the radon gas levels measured in the scintillation cell 74.

Current continuous air monitors typically use very high flow rates of on the order of 1 cfm (32 lpm) or greater. Much of the reason for these high flow rates is to provide enough counts so that meaningful statistical calculations can be performed in order to eliminate the radon daughter interference counts. In order to have a 95% confidence that the counts accumulated in a 30 minute period are within 20% of the actual activity (determined over a very long period of time), a counting rate of about 3.3 cpm is required when there are not any interfering background counts present in the energy areas of interest. The flow rate required to achieve a filter activity for plutonium of about 3.3 cpm after an accumulation of 8 DAC-hrs, is 1.5 lpm. Because counting efficiencies are typically of on the order of only about 30%, however, the flow rate must be increased to about 5 lpm. Best results are achieved when each filter individually is able to contribute a minimum count level of about 3.3 cpm. Since the flow duty cycle (i.e., ratio of active:inactive time periods) is about 50%, an additional flow increase to 10 lpm would provide optimal results.

Flow rates of about 10 lpm not only reduce the air vacuum requirements, but the minimum 2:1 (and sometimes as much as 5:1) reduction in air flow over current implementations reduces filter packing problems to similar extents. Since each of the two filters is inactive for about half of the time of monitor operation, the reduction of filter packing that can be experienced is on the order of about 4:1 or greater. This significant reduction in filter packing eliminates one of the major sources of excessively wide emission spectrum tails that interfere with the effectiveness of multi-channel analyzer sampling. In addition, the requirement of routine maintenance can be reduced in frequency.

There are two principal forms of analysis that are performed continuously by the processor 38. The analysis is done continuously because it is desirable to generate an alarm condition as soon as it can be determined that an alarm condition exists. The first analysis section deals with the active filter (hereinafter "A") through which air is being drawn. The second analysis section deals with the inactive filter(s) (hereinafter "I") through which no air is being drawn and the short-lived elements are being allowed to decay.

Active filter (A) analysis pertains to analysis of only a single filter at a time, whereas inactive filter (I) analysis pertains to the analysis of one or more filters at a time. The length of each analysis period corresponds to the length of the "on" times and the "off" times for air sampling by each individual filter. Active or inactive filter analysis occurs at any given moment during operation of the monitoring device. The length of the "on" and "off" cycles is a function of length of the total test cycle and the number of filters used. For a test time T and number of filters N, the length of the active filter period is T/N. The length of the inactive filter period is $T*(N-1)/N$. For a two filter system with a 90 minute cycle time, both the A and I periods will be 45 minutes. For a three filter system with a 90 minute cycle time, the A period will be 30 minutes and the I period will be 60 minutes.

Figure 12:
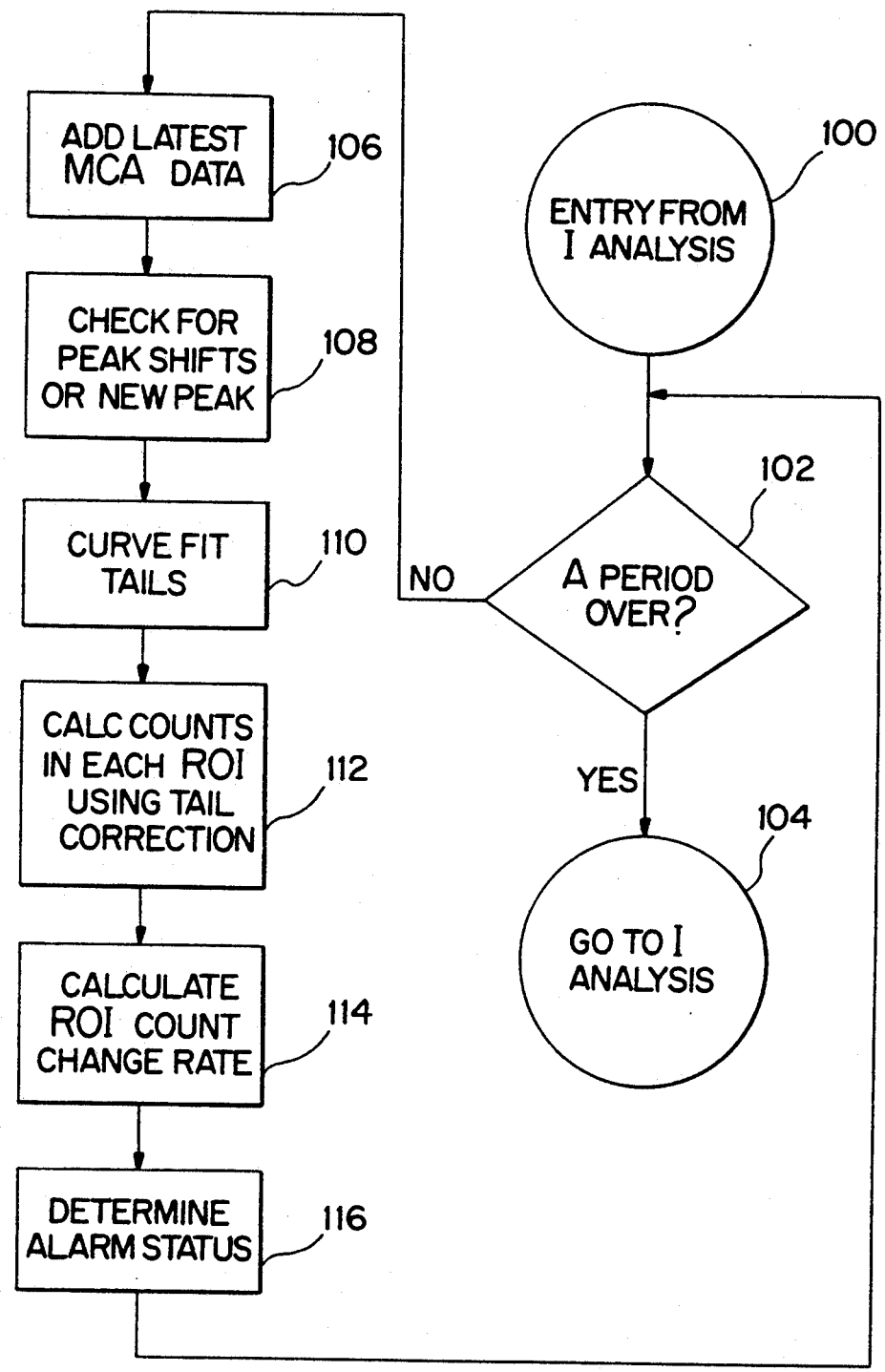
FIG. 12 is a flow chart illustrating the operation of the active filter portion of the invention.
Figure 13:
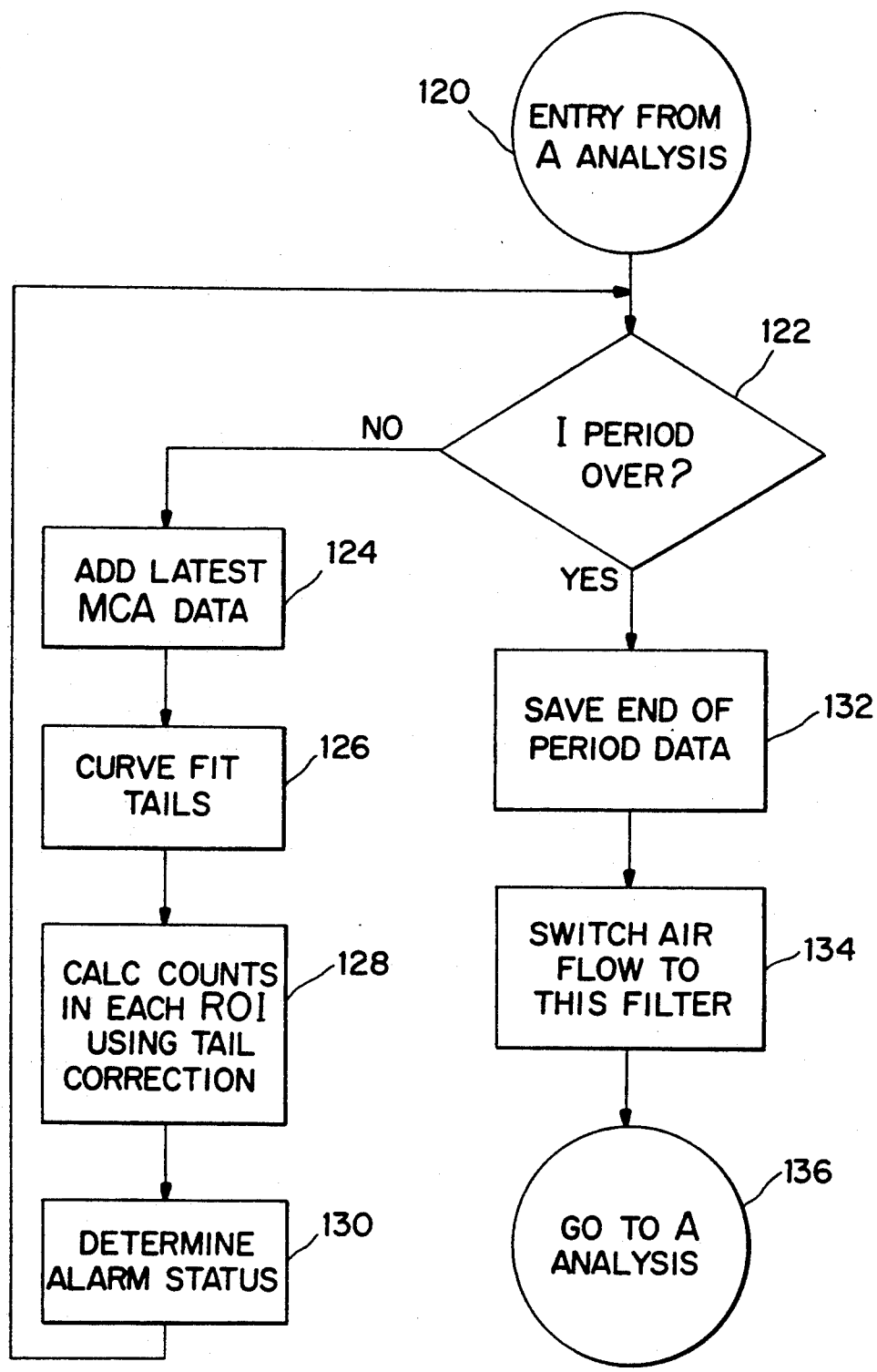
FIG. 13 is a flow chart illustrating the operation of the inactive (no air flow) portion of the invention.

FIG. 12 shows a flow chart for active filter (A) analysis, whereas FIG. 13 shows a flow chart for inactive filter (I) analysis.

In the active (A) filter analysis, which incorporates the processing steps as illustrated in FIG. 12, air is drawn through a predetermined one of the filters 48, 50 (FIG. 9). Radioactive elements are collected on the filter, and the activity on the filter increases at a rate dependent upon: 1) the amount of each radioactive element present in the air; 2) the half-lives of the elements collected on the filter; and 3) the rate of air flow.

As noted previously, the continuous air monitoring system of the present invention processes data in accorance with an active (A) filter analysis and an inactive (I) filter analysis. Therfore, upon completion of the active cycle analysis during the continual operation of the system, the system initiates the inactive cycle analysis, after which another cycle, such as another active analysis, is begun. With reference to block 100, the aforementioned alternating analysis arrangement is entered upon completion of a preceding inactive (I) period of analysis. As denoted by block 102, the first decision to be made in the active analysis involves a determination as to whether the time period previously established as the desired duration for the active (A) analysis cycle has elapsed. This determination can be made based upon timing data or clock input to the processor 38. If the prescribed time period has expired, as indicated by block 104, then the system exits the active analysis mode and enters the inactive analysis mode illustrated by FIG. 13. The specific procedures involved in the inactive analysis as shown in FIG. 13 will be discussed in more detail below. However, if the duration time period for the active analysis has not expired, the multi-channel analyzer (MCA) measures the amount of activity within each energy channel and makes that data available on a continuous basis to the processor 38 for processing thereby. This data is totalled in the processor with other parameters measured previously by the MCA, as indicated by block 106.

As indicated by block 108, the data measured by the MCA is analyzed by the processor in order that peaks such as 20, 22, and 24 of FIG. 7 can be located and identified. A region of interest (ROI) around each peak is determined. The leftwardly-extending curve from each of the major peaks (such as that extending from peak 20) is curve-fitted to a general exponential equation form as denoted by block 110. The area under a tail that extends into a neighboring region to the left of the peak is integrated, as indicated by block 112, to determine the activity contribution in that region from the tail portion of the ROI. This activity is generally considered as "background" or "interference" activity. Longer term background data for each ROI has preferably been stored from calculations made during the previous periods of inactivity (I) for the filter.

Following determination of the background count rate in the foregoing manner, the rate of count change for the ROI is calculated by subtracting the background activity from the total measured activity in the ROI, as indicated by block 114. The rate of activity increase is calculated in addition to the current activity for this period of activity. The net activity rate is then compared at the processor with a predetermined alarm rate threshold stored in addressable memory associated with the processor, as indicated at block 116, and an appropriate alarm signal is generated if the measured activity rate meets or exceeds the predetermined threshold. Because of the dynamic nature of the radioactive elements in the air and the resulting changes continuously occurring on the filter during active air flow, the period during which air is flowing through the filter, the active period, is the period of least sensitivity for the particular filter. The sequence of steps discussed above is repeated for the duration of the active filter (A) analysis period. When the active period is over, the air flow to that filter is terminated, and the inactive (i.e., non-air flow) period (I) for that filter is initiated, as illustrated by block 104.

With reference to FIG. 13, there is depicted the inactive period (I) analysis. This period of analysis resembles that of the active period (A) analysis previously discussed and depicted in FIG. 12, with the exception that the activity of the short term decay products is continually decreasing, as shown in FIG. 3. As the long term decay products exhibit half-lives many orders of magnitude longer than those of the short term decay products, there is no perceptible decrease in the activity of long term decay products, as described previously in connection with FIG. 4. As the peak activity of the short term decay products lessens, the sensitivity to the long term activity increases as the "tail" portion of each isotope's energy spectrum diminishes in size. The necessity for, and magnitude of, background corrections diminish during this period, and the uncertainty associated with the background or interference activity decreases in absolute terms.

The procedural steps involved in the inactive (I) analysis of FIG. 13 have corresponding steps to the active (A) analysis depicted in FIG. 12 and described above. Accordingly, these corresponding steps are described in summary fashion below. As block 120 of FIG. 13 indicates, the inactive (I) analysis is entered upon completion of the active (A) analysis. A determination is then made in accordance with time data input to the processor 38 as to whether the prescribed interval for the inactive (I) period has lapsed, as indicated by block 122. If the duration of the time period established for the inactive (I) analysis has not expired, then the series of processing steps indicated by blocks 106, 110, 112 and 116 of FIG. 12 are performed during the inactive (I) analysis as illustrated by corresponding blocks 124, 126, 128 and 130, respectively, of FIG. 13. The duration of each filter sampling period and the number of filters to be evaluated is selected to ensure a suitable sampling period towards the end of the inactive (I) analysis mode, where the activity in the ROI of the particular elements of interest can be determined with virtually no background influence with which to contend.

However, if the duration of the period established for the inactive (I) analysis has expired, then the data for that filter is stored in processor memory for recall, as indicated by block 132 of FIG. 13, and used in correction calculations in the active period (A) mode of analysis. Thereafter, the air flow to the filter is resumed, as indicated by block 134, and the monitoring device shifts to another mode of analysis, such as the active (A) mode, as shown by block 136.

EXAMPLE 1

The first illustration assumes that it is desired to have a 0.002 pCi/l Pu detection level averaged over a period of about 8 hours (this is an 8 DAC-hr spec), in the presence of 0.01 WL (2 pCi/l) of radon progeny. It is assumed for simplicity of illustration that only $^{239}$Pu is present and that the multi-channel analyzer is sufficiently tuned so that RaA is the only interfering isotope.

A continuous flow monitor of the subject invention employing dual filters is preferably used. A flow rate of 10 lpm is alternately applied to one filter and then the other, switching modes every 45 minutes. Table IV below is constructed so as to show the counts for $^{239}$Pu and $^{218}$Po (RaA) for each 15 minute period. The counts for each of these elements during any period would be the integral of the appropriate ramp-up or ramp-down equations (Equations 1 and 3, respectively) that are applicable during active (A) and inactive (I) modes of filter analysis. Because no detector is 100% efficient, adjustments must be made to account for detector inefficiencies. In the subject invention, detectors having an efficiency of about 30% are utilized. Therefore, count rate data measured by each detector is interpolated to arrive at the count rates (cpm) listed in Tables IV and V. During the last thirty minutes of the ten hour operating period, there is a Pu count rate of 11.9 cpm. This count rate is in the presence of virtually no RaA background activity due to the comparitively much shorter RaA half-life, and will consequently constitute a highly accurate reading of the plutonium accumulation. At the end of the ten hour period, the Pu level will have reached the preselected alarm threshold of approximately 12 cpm. Upon the attainment of alarm threshold, at least one or more of the following measures is preferably implemented: 1) generation of an audible alarm; 2) generation of a visually perceptible alarm; and/or 3) implementation (preferably automatic) of emergency measures (sealing of doorways, etc). It should be noted at this point that as a result of the linear relationship between the utilized flow rate and the time needed to reach a specified threshold, a threshold of approximately 12 cpm may be ascertained in eight hours by increasing the flow rate from about 10 lpm to about 12 lpm.

TABLE IV

RaA and Pu Build-up in Two Head Monitoring Filter A: 0.002 pCi/l Pu Concentration

| Mins. after Start | Pu CPM | RaA CPM | Motor | Mins. after start | Pu CPM | RaA CPM |
|---|---|---|---|---|---|---|
| 0 | 0 | 0 | OFF | | | |
| 15 | 0.7 | 22 | ON | 285 | 6.6 | 22 |
| 30 | 1.3 | 22 | | 300 | 7.3 | 22 |
| 45 | 2.0 | 22 | | 315 | 7.9 | 22 |
| 60 | 2.0 | 1 | OFF | 330 | 7.9 | 1 |
| 75 | 2.0 | 0 | | 345 | 7.9 | 0 |
| 90 | 2.0 | 0 | | 360 | 7.9 | 0 |
| 105 | 2.6 | 22 | ON | 375 | 8.6 | 22 |
| 120 | 3.3 | 22 | | 390 | 9.2 | 22 |
| 135 | 4.0 | 22 | | 405 | 9.9 | 22 |
| 150 | 4.0 | 1 | OFF | 420 | 9.9 | 0 |
| 165 | 4.0 | 0 | | 435 | 9.9 | 1 |
| 180 | 4.0 | 0 | | 450 | 9.9 | 1 |
| 195 | 4.6 | 22 | ON | 465 | 10.6 | 22 |
| 210 | 5.3 | 22 | | 480 | 11.2 | 22 |
| 225 | 5.9 | 22 | | 495 | 11.9 | 22 |
| 240 | 5.9 | 1 | OFF | 610 | 11.9 | 1 |
| 255 | 5.9 | 0 | | 625 | 11.9 | 0 |
| 270 | 5.9 | 0 | | 640 | 11.9 | 0 |

EXAMPLE 2

The conditions of this second illustration are the same as those in the first illustration, with the exception that the plutonium concentration is doubled to 0.004 pCi/l. The filter activity is shown in Table V. In this example, the preselected alarm threshold of about 12 Pu cpm is reached after an elapsed time of only about four hours.

TABLE V

RaA and Pu Build-up In Two Head Monitoring Filter A: 0.004 pCi/l Pu Concentration

| Mins. after Start | Pu CPM | RaA CPM | Motor | Mins. after start | Pu CPM | RaA CPM |
|---|---|---|---|---|---|---|
| 0 | 0 | 0 | OFF | | | |
| 15 | 1.2 | 22 | ON | 285 | 13.2 | 22 |
| 30 | 2.6 | 22 | | 300 | 14.6 | 22 |
| 45 | 4.0 | 22 | | 315 | 15.8 | 22 |
| 60 | 4.0 | 1 | OFF | 330 | 15.8 | 1 |
| 75 | 4.0 | 0 | | 345 | 15.8 | 0 |
| 90 | 4.0 | 0 | | 360 | 15.8 | 0 |
| 105 | 5.2 | 22 | ON | 375 | 17.2 | 22 |
| 120 | 6.6 | 22 | | 390 | 18.4 | 22 |
| 135 | 8.0 | 22 | | 405 | 19.8 | 22 |
| 150 | 8.0 | 1 | OFF | 420 | 19.8 | 0 |
| 165 | 8.0 | 0 | | 435 | 19.8 | 1 |
| 180 | 8.0 | 0 | | 450 | 19.8 | 1 |
| 195 | 9.2 | 22 | ON | 465 | 21.2 | 22 |
| 210 | 10.6 | 22 | | 480 | 22.4 | 22 |
| 225 | 11.8 | 22 | | 495 | 23.8 | 22 |
| 240 | 11.8 | 1 | OFF | 610 | 23.8 | 1 |
| 255 | 11.8 | 0 | | 625 | 23.8 | 0 |
| 270 | 11.8 | 0 | | 640 | 23.8 | 0 |

It can be observed in the foregoing two examples that during each 90 minute period, there is a period in excess of 30 minutes for each filter during which a very accurate determination of the Pu concentration build-up can be made. Accurate Pu measurements are possible since the filter has been removed from the air flow for a sufficient time to allow the natural decaying process to substantially eliminate the existence of virtually all interfering background caused by the various alpha-emitting radon decay products that may have been present in the air supplied to the filter. Overall, for two filters, there is a period in excess of 60 minutes during each 90 minute time period during which very accurate plutonium counting can occur. It may also be observed from the two illustrations that the growth in the Pu concentrations is linear over time.

While the invention has been described in connection with specific embodiments thereof, it is to be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A continuous air monitoring system comprising:
   an air intake port;
   at least two air filtering means in fluid communication with the air intake port;
   selection means for selectively supplying air from the air intake port to a predetermined one or more of the filtering means;
   detection means positioned relative to the filtering means for measuring the level of radioactivity of particles collected by the selected filtering means; and
   control means associated with the selection means for controlling the supply of air from the air intake port to a predetermined at least one of said filtering means, said control means being operable to successively supply air from the air intake port to each of the filtering means for a predetermined time interval in accordance with a predetermined characteristic of a constituent of the air flow.

2. The continuous air monitoring system of claim 1, wherein the filtering means are aligned along substantially parallel planes downstream of the air intake port.

3. The continuous air monitoring system of claim 1, wherein negative pressure generating means is operable to draw air into the system and through at least one of said filtering means.

4. The continuous air monitoring system of claim 1, wherein the selection means comprises a valve assembly for permitting air flow from the air intake port through a selected one or more of the filtering means and for prohibiting air flow through non-selected filtering means.

5. The continuous air monitoring system of claim 4, wherein the valve assembly comprises at least two separate and distinct valves, at least one of said valves being positioned downstream of a corresponding one of the filtering means for allowing independent control of air flow through said filtering means.

6. The continuous air monitoring system of claim 1, further comprising a scintillation cell positioned in fluid communication with the air intake port for measuring the level of radon gas present in at least a portion of the air flowing through the monitoring system.

7. The continuous air monitoring system of claim 1, further comprising a charged particle air pre-filtering system positioned between said air intake port and at least one of said air filtering means.

8. A method of continuously monitoring an air flow for the presence of a radiation-emitting material, comprising the steps of:
   directing the air flow to a first filtering means for filtering thereby for a predetermined active time interval;
   terminating the air flow to the first filtering means following lapsing of the predetermined time interval;
   directing the air flow to a second filtering means for air filtering thereby for a second predetermined time interval;
   maintaining the first filtering means out of the air flow to be monitored for a predetermined inactive time interval and measuring the level of the radioactive activity present on the first filtering means; and
   terminating the air flow to the second filtering means and directing the air flow to the first filtering means, wherein the predetermined active time interval is established in accordance with the half-life value of a predetermined air flow element.

9. The method of claim 8, further comprising the step of measuring the level of radioactivity present on the second filtering means.

10. The method of claim 9, further comprising the step of measuring the level of radioactivity continuously of at least one of said filtering means.

11. The method of claim 8, wherein the steps ae sequentially repeated for a plurality of filtering means.

12. The method of claim 8, wherein the level of radioactivity of at least one of said filtering means is continuously measured for a predetermined time interval.

13. The method of claim 8, further comprising the step of comparing the levels of radioactivity measured from said first and second filtering means.

* * * * *